(12) United States Patent
Rustad et al.

(10) Patent No.: US 9,791,389 B2
(45) Date of Patent: *Oct. 17, 2017

(54) PRE-STRESSED GAMMA DENSITOMETER WINDOW AND METHOD OF FABRICATION

(71) Applicant: SCHLUMBERGER TECHNOLOGY CORPORATION, Sugar Land, TX (US)

(72) Inventors: Rolf Rustad, Bergen (NO); Paal Bratland, Bergen (NO); Jean-Francois Noel, Bergen (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/274,256

(22) Filed: Sep. 23, 2016

(65) Prior Publication Data

US 2017/0010225 A1 Jan. 12, 2017

Related U.S. Application Data

(63) Continuation of application No. 13/511,140, filed as application No. PCT/US2010/058581 on Dec. 1, 2010, now Pat. No. 9,455,483.

(Continued)

(51) Int. Cl.
*G01N 23/12* (2006.01)
*G01N 23/083* (2006.01)
(Continued)

(52) U.S. Cl.
CPC .............. *G01N 23/12* (2013.01); *G01F 1/74* (2013.01); *G01N 23/083* (2013.01); *H01P 1/08* (2013.01);
(Continued)

(58) Field of Classification Search
CPC ...... G01N 23/04; G01N 23/12; G01N 23/083; G01N 2223/04; G01N 2223/317; H01P 1/08; G01F 1/74
See application file for complete search history.

(56) References Cited

U.S. PATENT DOCUMENTS 3,437,950 A 4/1969 Okaya et al.
4,153,854 A 5/1979 Christgau et al.
(Continued)

OTHER PUBLICATIONS

International Search Report and Written Opinion issued in the related PCT application PCT/US2010/058581, dated Feb. 4, 2011 (9 pages).

(Continued)

*Primary Examiner* — David E Smith
(74) *Attorney, Agent, or Firm* — Cameron R. Sneddon

(57) ABSTRACT

A gamma densitometer window is provided along with a method of fabrication thereof. The window comprises a plate of non-metallic, preferably gamma transparent, material having a first face and a second face opposing one another and having an outer edge defined therebetween. The window further comprises a metallic frame member fitted around the outer edge of the plate and adapted to pre-load the plate with a compressive stress that is sufficiently high such that the sum of the compressive stress, tensile stress and shear stress components generated in the plate under high-pressure conditions is always compressive. The method of fabrication shrink fitting the metallic frame member around the outer edge of the plate at a shrink-fit temperature such that the metallic frame member applies a compressive stress to the plate at any temperature below the shrink-fit temperature.

20 Claims, 3 Drawing Sheets

Related U.S. Application Data

(60) Provisional application No. 61/265,663, filed on Dec. 1, 2009.

(51) Int. Cl.
*H01P 1/08* (2006.01)
*G01F 1/74* (2006.01)

(52) U.S. Cl.
CPC ... *G01N 2223/04* (2013.01); *G01N 2223/317* (2013.01); *Y10T 29/49865* (2015.01)

(56) References Cited

U.S. PATENT DOCUMENTS

| | | |
|---|---|---|
| 4,179,037 A | 12/1979 | Chan et al. |
| 4,306,155 A | 12/1981 | Cotic |
| 4,738,064 A | 4/1988 | Aarts et al. |
| 4,788,852 A | 12/1988 | Martin et al. |
| 5,025,160 A | 6/1991 | Watt |
| 5,689,540 A | 11/1997 | Stephenson et al. |
| 5,732,166 A | 3/1998 | Hamann et al. |
| 6,154,946 A | 12/2000 | Kapp |
| 6,265,713 B1 * | 7/2001 | Berard .............. G01F 1/363 250/269.1 |
| 6,335,959 B1 | 1/2002 | Lynch et al. |
| 6,405,604 B1 | 6/2002 | Berard et al. |
| 7,105,805 B2 | 9/2006 | Berard et al. |
| 7,240,568 B2 | 7/2007 | Atkinson |
| 7,978,815 B2 * | 7/2011 | Tjugum .............. G01N 9/24 378/54 |
| 9,455,483 B2 * | 9/2016 | Rustad .............. H01P 1/08 |
| 2004/0080387 A1 | 4/2004 | Denis et al. |
| 2006/0180141 A1 | 8/2006 | Schnell et al. |
| 2007/0124091 A1 * | 5/2007 | Wee .............. G01F 1/58 702/49 |
| 2009/0147907 A1 | 6/2009 | Wraight |
| 2010/0046714 A1 * | 2/2010 | Sikora .............. B08B 3/04 378/140 |
| 2012/0256086 A1 * | 10/2012 | Husebo .............. G01N 9/24 250/307 |

OTHER PUBLICATIONS

International Preliminary Report on Patentability issued in the related PCT application PCT/US2010/058581, dated Jun. 5, 2012.

\* cited by examiner

PRE-STRESSED GAMMA DENSITOMETER WINDOW AND METHOD OF FABRICATION

CROSS-REFERENCE TO RELATED APPLICATION

This patent application is a continuation of co-pending U.S. patent application Ser. No. 13/511,140, now U.S. Pat. No. 9,455,483, which application claims the benefit and priority of provisional application, U.S. Ser. No. 61/265,663, filed Dec. 1, 2009, which the contents of each are incorporated herein by reference.

BACKGROUND

Field

The present invention generally relates to gamma-transparent non-metallic windows used in the densitometry of pressurized fluids, and to gamma densitometers containing such windows. It is particularly concerned with a ceramic window that has been pre-loaded with compressive stress via a shrink-fitting fabrication method to better resist tensile stresses generated under high-pressure conditions.

Description of the Related Art

Gamma densitometry is a method used to characterize and measure properties of fluids or mixtures of fluids in many applications, including the oil and gas industry. Gamma densitometers are used in such methods. Typical applications of gamma densitometry and apparatus using the gamma densitometry method include level gauges for measuring fluid levels in tanks and separator vessels, densitometers for measuring the density of liquids in a pipe, and densitometers for measuring gas fraction in a multi-phase fluid flow. A special type of gamma densitometer is the dual-energy gamma densitometer. This apparatus uses gamma radiation of different wavelengths to simultaneously measure several properties of a fluid or mixture of fluids. It is typically used to measure the gas fraction and water cut simultaneously in a multi-phase well effluent. Such measurements are often performed on fluids under harsh conditions, such as high pressure and high temperature, for example, in a flow pipe, in a separator vessel, in a venturi, or some other pressure-containing body or vessel.

When a gamma densitometer is to be used to measure properties of fluids under pressure it is necessary to create an aperture in the pipe or pressure vessel that is transparent or nearly transparent to gamma radiation, but which still can function as a pressure barrier and withstand the high stresses experienced in such environment. Such an aperture is commonly known as a "gamma window." If the gamma radiation is of a short wavelength, and hence high energy, such a window may be made from metal, or indeed be just a section of the pipe or the pressure vessel wall. Gamma radiation of lower energy, in particular energies lower than a few hundred KeV, is easily stopped by a few millimeters of metals. A notable exception is the metal beryllium, which is highly transparent to gamma radiation even at very low energies. However, this metal is highly prone to corrosion, and thus is not an ideal candidate for use for gamma windows in many applications.

Consequently, such "gamma windows" are commonly manufactured from ceramic materials. There are several ceramic materials that may be used to manufacture gamma windows since they combine high strength, in particular in compression, and low attenuation of gamma radiation. Unfortunately, such ceramic materials are brittle, i.e., they can support high compressive loads, but much smaller tensile and shear loads. This property makes gamma windows manufactured from ceramic materials prone to failure in high-pressure applications where the pressure applied by the fluid to the face of the window generates tensile and shear stresses that the non-metallic material forming the window cannot withstand.

It is therefore desirable to provide an improved pressure and temperature resistant window for gamma densitometry and other applications, and preferably a window that is transparent or nearly transparent to gamma radiation.

SUMMARY

The present disclosure advantageously provides a gamma densitometer window for a gamma densitometer that is preferably resistant to failure under high-pressure applications. To this end, the gamma densitometer window of the present disclosure comprises a plate of non-metallic, preferably gamma transparent, material having a first face and a second face opposing one another. The first face and the second face of the plate has an outer edge defined therebetween. The gamma densitometer window further comprises a metallic frame member fitted around the outer edge of the plate and adapted to pre-load the plate with a compressive stress that is sufficiently high, such that the sum of the compressive stress, and tensile and shear stress components generated in the plate under high-pressure conditions is always compressive.

Furthermore, such construction ensures that the non-metallic material forming the plate is always kept in compression, i.e. it is only exposed to compressive stress, and not to tensile. This is accomplished, at least in part by pre-compressing the non-metallic material through the manufacturing process known as "shrink-fitting."

The plate forming the window may be circular and the surrounding metallic frame member may have an annular inner diameter that receives and compresses the outer edge of the plate to uniformly pre-load the plate with compressive stress around its circumference. Preferably, the metallic frame member is tubular and is mounted in or on the pressure-bearing side of a wall of the pressurized fluid-containing body, e.g., a pipe or pressure vessel, such that pressure applied by the fluid is applied to the outer diameter of the frame member and increases the amount of compressive stress the frame member applies around the plate. Such a structural arrangement results in the "self energizing" sealing and stress compensation mechanism of the gamma ceramic window.

The metallic tube may include an annular shoulder that supports an outer portion of a non-pressure bearing face of the plate to increase the retentiveness of the frame member around the plate. Additionally, an interface may be interposed between the inner diameter of the metallic frame member and the outer edge of the plate. The interface is preferably formed of softer metal than the frame member, such that when the frame member applies compressive stress around the circular plate, the interface deforms in order to uniformly equilibrate the stress around the circumference of the plate. The interface may have an annular rim that supports an outer portion of a non-pressure bearing face of the plate in order to assist the annular shoulder in increasing the retentiveness of the frame member around the plate.

In the method of fabricating a gamma densitometer window described herein, the parts are manufactured with dimensions and tolerances such that at room temperature the outer diameter of the non-metallic plate is slightly larger than the inner diameter of the metallic frame member. The fabrication method preferably comprises the steps of: providing a plate of non-metallic material having a first face and a second face opposing one another and having an outer edge defined therebetween; providing a metallic frame member having an inner periphery that is complementary in shape but slightly smaller than the outer edge of the plate at an ambient temperature; and shrink-fitting the metallic frame member around the outer edge of the plate at a shrink-fit temperature such that the metallic frame member applies a compressive stress to the plate at any temperature below the shrink-fit temperature.

Shrink fitting may be accomplished by heating the metallic frame member until thermal expansion renders its inner diameter slightly larger than the outer diameter of the plate. The plate is next inserted within the inner diameter of the frame member, whereupon the metallic member is allowed to cool to ambient temperature. The resulting thermal contraction causes the metallic frame member to pre-load the outer edge of the plate with compressive stress. In one embodiment, the frame member is formed of steel and is dimensioned such that substantial compressive stress is generated within the plate as a result of such shrink fitting.

BRIEF DESCRIPTION OF THE DRAWINGS

Implementations of the present disclosure may be better understood when consideration is given to the following detailed description thereof. Such description makes reference to the annexed pictorial illustrations, schematics, graphs, drawings, and appendices. In the drawings.

DETAILED DESCRIPTION

Various embodiments and aspects of the present disclosure will now be described in detail with reference to the accompanying figures. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited. Further, whenever a composition, a group of elements or any other expression is preceded by the transitional phrase "comprising," "including" or "containing," it is understood that it is also contemplated the same composition, the group of elements or any other expression with transitional phrases "consisting essentially of," "consisting," or "selected from the group of consisting of," preceding the recitation of the composition, the elements or any other expression.

Ceramic materials typically have poor flexural and tensile strength, while the compressive strength is much higher. A way to overcome the problem of the low flexural or tensile strength, is to pre-load the ceramic with a high compressive stress. When a ceramic is used as part of a pressure design, as is the case for gamma radiation windows, it is necessary to pre-load the ceramic with a compressive stress sufficiently high that the sum of any tensile stress produced by the fluid pressure, and the compressive stress produced by the pre-loading, is always compressive.

Figure 1:
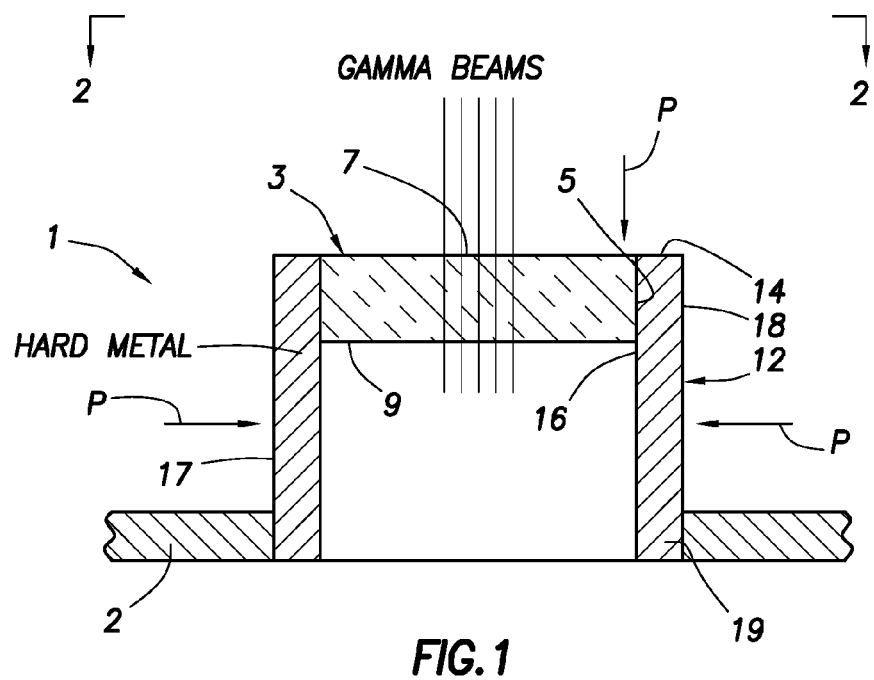
FIG. 1 depicts a cross-sectional side view of a first embodiment of the gamma window of the present disclosure.
Figure 2:
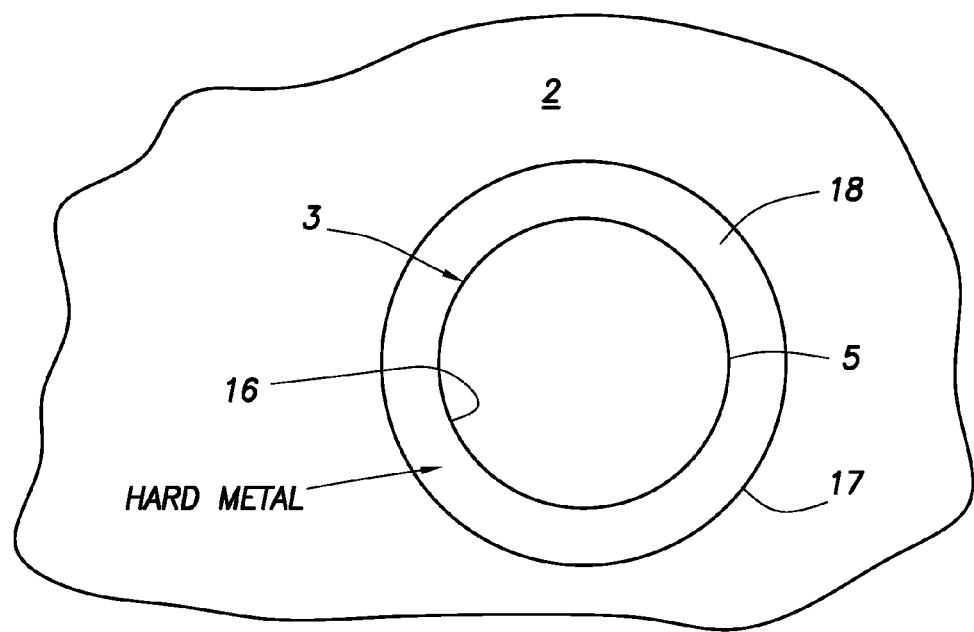
FIG. 2 depicts a plan view of the gamma window illustrated in FIG. 1 taken along the line 2-2.

FIGS. 1 and 2, illustrate an example of the gamma window 1 of the present disclosure, which is shown in FIG. 1 as being mounted onto a pressure-bearing wall 2 in alignment with a source of gamma radiation (not shown). The gamma window 1 includes a plate 3, preferably constructed from a non-metallic material such as a ceramic material or diamond, having a circular outer edge 5, a pressure-bearing face 7 that contacts the pressurized fluids being measured or sensed, and a non-pressure bearing face 9. In use, the pressure bearing face 7 faces a gamma ray source. The gamma window can be made from ceramic materials such as boron carbide (B4C), boron nitride, diamond, synthetic diamond and silicon carbide. The front surface of the gamma window is smooth, and can be either flat or shaped to match the geometry in which it is installed. Typical thicknesses range from 2 mm to 15 mm and diameters vary from 4 mm to 50 mm. The gamma window 1 further includes a metallic frame member 12 formed, in this example, from a steel tube 14 having a length that is longer than the thickness of the plate 3. The inner diameter 16 of the tube 14 of the frame member 12 is complementary in shape but slightly smaller than the circular outer edge 5 of the plate 3 so that the frame member 12 compressively pre-loads all points of the circular plate 3 with compressive stress. The outer diameter 17 of the tube 14 is exposed to the pressurized fluid confined by the pressure-bearing wall 2 as indicated by the arrow P. The temperature of the pressurized fluid may also be determined through the gamma window 1. The distal end 18 of the tube 14 circumscribes and retains the plate 3 by frictional forces, while the proximal end 19 of the tube is sealingly mounted to the wall 2. The metal part of the present disclosure utilizes high strength material, typically high strength Nickel alloys, cobalt alloys or high strength stainless steels.

In operation, when pressurized fluid is confined by the wall 2, the resulting pressure not only presses against the face 7 of the plate 3, but also acts against the outer diameter of the tube 14 forming the frame member, thereby increasing the compressive stress applied around the outer edge 5 of the plate 3 and further increasing the frictional grip between the outer edge 5 and the inner diameter 16 of the tube 14, the gamma window is designed to operate at pressures up to 60000 psi/4137 bar. Thus the gamma window 1 is self-energizing. It is important to note that the relative dimensions between the diameter of the outer edge 5 of the plate 3 and the inner diameter of the tube 14 as well as the strength of the steel or other metal forming the tube 14 are chosen such that the sum of all stresses (i.e. tensile, shear and compressive) applied to the plate is always compressive during the operation of the gamma window 1. This way, the bending stress from the applied pressure is not given the opportunity to create tensile stress, which may fracture the plate 3. In at least one embodiment, the plate is compressively pre-loaded to overcome the tensile stress generated in/on the plate by pressure applied to at least one of the first and/or second faces, for example when exposed to the pressurized fluid.

Figure 3:
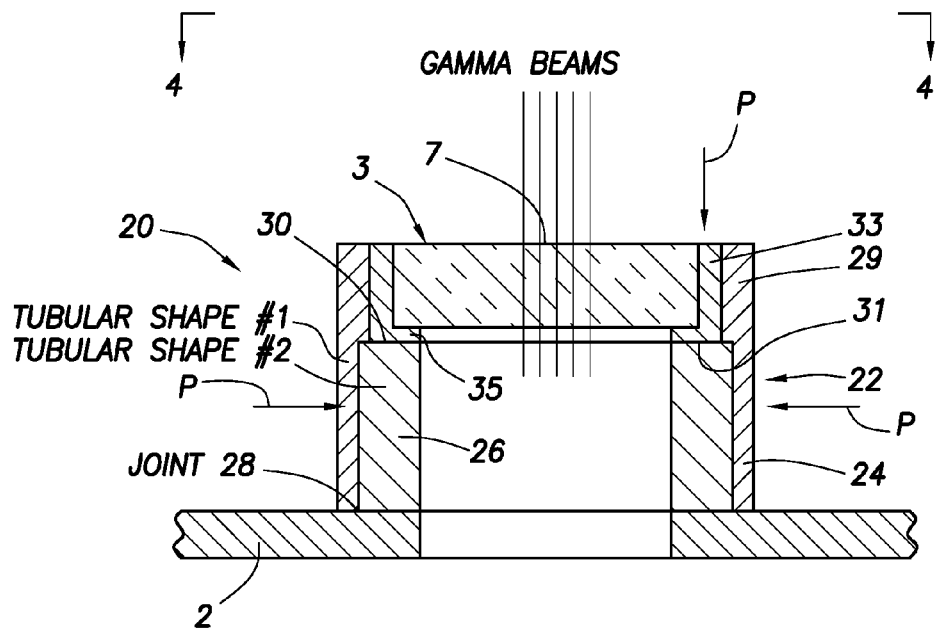
FIG. 3 depicts a cross-sectional side view of a second embodiment of the gamma window of the present disclosure.
Figure 4:
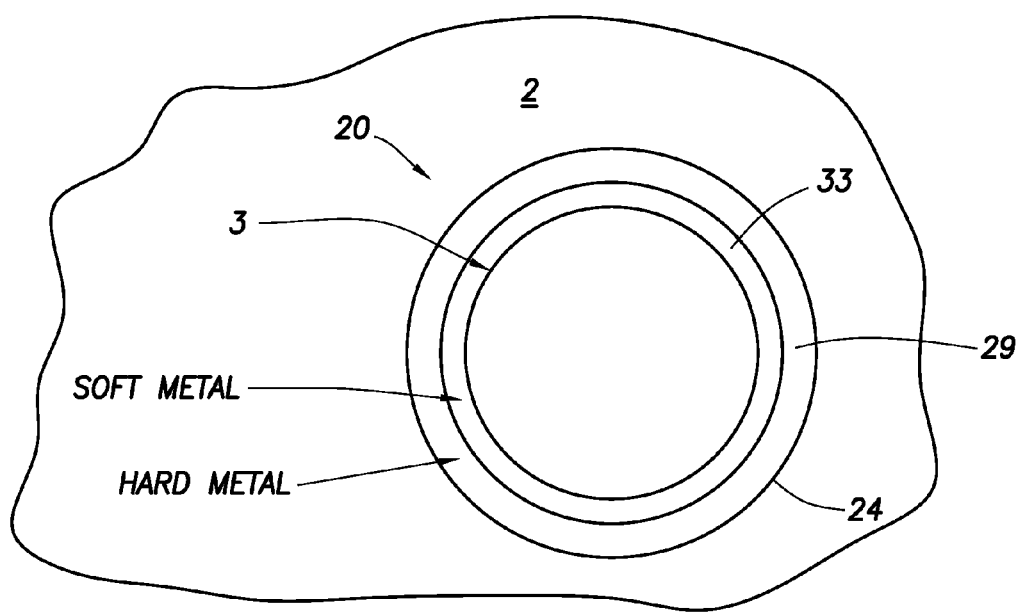
FIG. 4 depicts a plan view of the gamma window illustrated in FIG. 1 taken along the line 4-4.

FIGS. 3 and 4 illustrate a second embodiment 20 of the gamma window having greater pressure-resisting capability than the first embodiment 1. In this second embodiment, the metallic frame member 22 includes an outer tube 24 (which may be referred to as the first tubular shape) that tightly and concentrically overlies an inner tube 26 (which may be referred to as the second tubular shape). The tubes 24 and 26 are joined together via a weld joint 28 which may be formed by various suitable joining methods, such as welding, electron beam welding, or laser beam welding. The distal end 29 of the outer tube 24 extends over the distal end 30 of the inner tube 26 such that the distal end 30 of the inner tube 26 defines a supporting shoulder 31. The provision of the supporting shoulder 31 substantially increases the capability of the metallic frame member 22 to support the plate 3 under high-pressure conditions.

In addition to the supporting shoulder 31, the metallic frame member 22 further includes an annular interfacing layer 33 disposed between the plate 3, the inner diameter of the outer tube 24, and the support shoulder 31. The interfacing layer 33 is advantageously formed from a metal that is softer than the metal forming at least the outer tube 24 of the metallic frame member such that it deforms slightly when subjected to the compressive pre-load applied by the distal end 29 of the outer tube 24. Such deformation of the interfacing layer 33 insures that the compressive preload applied around the circumference of the outer edge 5 is substantially uniform at all points. Additionally, the interfacing layer 33 includes an annular rim 35 disposed between the support shoulder 31 and the outer portion of the plate 3 to provide further retention of the plate 3 in response to fluid pressure applied to plate face 7. The material of the interfacing layer is much softer than the ceramic and the hard metal used in the inner tube 26 and outer tube 24, but not so soft that it flows out of the opening between the two. A suitable material of the interfacing layer may be gold, platinum, palladium, tantalum, iridium or nickel.

Like the previously described first embodiment 1, when pressurized fluid is confined by the wall 2, the resulting pressure not only presses against the face 7 of the plate 3, but also acts against the outer diameter of the outer tube 24 forming part of the frame member 22, thereby increasing the compressive stress applied around the outer edge 5 of the plate 3 and further increasing the frictional grip between the outer edge 5 and the interfacing layer 33 and the inner diameter of the distal end 29 of the outer tube 24. Thus the gamma window 20 is self-energizing. Of course, the relative dimensions between the diameter of the outer edge 5 of the plate 3, the interfacing layer 33, and the inner diameter of the distal end of the tube 24 as well as the strength of the steel or other metal forming the tube 24 are chosen such that the sum of all stresses (i.e. tensile, shear and compressive) applied to the plate 3 is always compressive during the operation of the gamma window 20.

In the fabrication method of the first embodiment 1, the metal has a higher thermal expansion than the ceramic. The parts of the window are manufactured with dimensions and tolerances such that the inner diameter 16 of the tube 14 is smaller than the outer diameter 5 of the plate 3 at ambient temperature, where the ambient temperature is defined as the environment where the frame member is used, but excluding the environment where the frame member is manufactured. For example, the ambient temperature may be in the range of about −100° C. to about 300° C. The difference between these diameters at ambient temperature is known as interference. The amount of interference determines the pre-loading of the plate 3. The strength of the steel forming the tube 14 will ultimately limit the amount of pre-loading that can be created.

The tube 14 is heated to a temperature that increases the size of the inner diameter 16 via thermal differential expansion to an extent that allows the plate 3 (which is kept at a much lower temperature) to be inserted into the inner diameter 16. If the metal is heated too much, it may pass a phase transition temperature and change its properties. In the current embodiment of the present disclosure the temperature of the metal throughout the process should advantageously be controlled to ensure that this does not occur and that the properties of the metal do not change. In the case of high strength steel as well as other candidate high strength nickel and cobalt alloys, exposure to heating above 500° C. may impact the mechanical properties of the material, the significance of the impact being related to the length of the exposure. The local heating of the metal may be achieved in any suitable manner, e.g., through induction heating. The assembly may be facilitated by the use of assembly fixtures and jigs to avoid handling of very hot parts. The tube 14 and plate 3 are then allowed to cool back to ambient temperature, thereby shrink-fitting the plate 3 to the inner diameter 16 of the tube 14. The resulting contraction of the tube 14 forming the metallic frame member 12 pre-loads the outer edge 5 of the plate with the aforementioned desired amount of compressive stress.

In the fabrication method of the second embodiment, the inner and outer tubes 24 and 26 are precisely assembled through a transitional fit. The inner diameter of the portion of the outer tube 24 surrounding the inner tube 26 is chosen to be slightly larger or identical to the outer diameter of the inner tube 26 at ambient temperature. The outer tube 24 is assembled with the inner tube 26, and kept in place before welding using a fixture jig to ensure the required fit up, shown in FIG. 3.

The two tubes 24, 26 are then joined at the lower end via weld 28. This can be achieved by various joining methods including but not limited to TIG welding, electron beam welding, and laser beam welding.

When no interfacing layer 33 is used, the metallic part (outer and inner tubes 24 and 26) is heated to the required temperature, and the plate 3 is inserted into the inner diameter of the distal end 29 of the outer tube 24 so that the plate 3 rests on the top end of the inner tube 26. Cooling to lower temperatures achieves the shrink-fit as described above with regard to the plate 3 and the ring-shaped distal end 29 of the outer tube 24. The plate 3 is now held in place by shrink-fit forces and the frictional forces between the plate 3 and the metal of the distal end 29 of the outer tube 24. The plate 3 is further supported by the end of the inner tube 26, so that when the window 20 is exposed to pressure in the direction indicated in FIG. 3 by an arrow, the plate 3 will rest on the end of the inner tube 26 and thus be held in place.

The design of the outer tube 24 allows its distal end 29 to act as a ring, which is compressed around the outer edge 5 of the plate 3 when the window 20 is exposed to pressurized fluid. Immediately beneath the distal end 29 the outer tube 24 has a thinner wall, facilitating the compressive, radially inward motion of the ring-shaped distal end 29. This is the "self-energizing" sealing and stress-compensating feature of the design. Below the transition point between the distal end 29 and the thinner wall of the outer tube 24, the thinner wall is supported by the outer wall of the inner tube 26 in such a way that it is not deformed even at very high pressures.

When an interfacing layer 33 is provided in the second embodiment 20, the outer and inner tubes 24, 26 are attached to one another in the position illustrated in FIG. 3 by transitional fit and welding. Next, the interfacing layer 33 is applied around the inner diameter of the distal end 29 of the outer tube 24 and over the support shoulder 31 of the inner tube 26. The material of the interfacing layer 33 is selected so that the forces exerted on it during the shrink-fit process will allow it to deform. In this embodiment 20, the top part of the outer tube 24 has an inner diameter, which is larger than the outer diameter 5 of the plate 3 to provide room for the interfacing layer 33.

The soft metal forming the interfacing layer 33 may be deposited onto the hard metal forming the outer and inner tubes 24, 26 through a variety of methods including but not limited to vapor deposition, electroplating, or fusion with a preformed shape. After the soft metal of the interfacing layer 33 has been deposited onto the indicated surfaces, it is machined to have an inner diameter, which at room temperature and the intended operating temperatures is smaller than the diameter of the outer edge 5 of the plate 3.

A shrink-fit between the plate 3 and the interfacing layer 33 is next achieved in the same manner as described before. The tubes 24, 26 and the interfacing layer 33 are heated such that the inner diameter of the interfacing layer becomes large enough via thermal expansion to receive the plate 5. The resulting gamma window 20 is allowed to cool to ambient temperature, whereupon the resulting thermal contraction shrink-fits all of the aforementioned components 3, 33, 24 and 26 together in a frictional or interference type fit. The plate 3 is now held in place by the shrink-fit forces and the frictional forces between the plate 3 and the interfacing layer 33. The soft metal forming the interfacing layer 33 will be deformed by the pressure exerted by the hard metal forming the outer tube 24 as it contracts through cooling. This will cause the soft metal to flow, and it will fill any microscopic corrugations on the surface of the outer edge 5 of the plate 3 or the surfaces of the inner diameter of the distal end 29 of the outer tube 24. Such metallic flow reduces local stress concentrations at the surface of the plate 3 caused by imperfections in the surface finish of the metal tube 24, and improves the seal between the ceramic and the metal, essentially making the seal helium leak tight, or hermetic. The plate 3 is further supported by the support shoulder 31 of the inner tube 26 and the rim 35 of the interfacing layer 33 so that when the gamma window 20 is exposed to pressure in the direction indicated in FIG. 3, the plate 3 will rest on the end of the inner tube 26 and thus be held in place.

Figure 5:
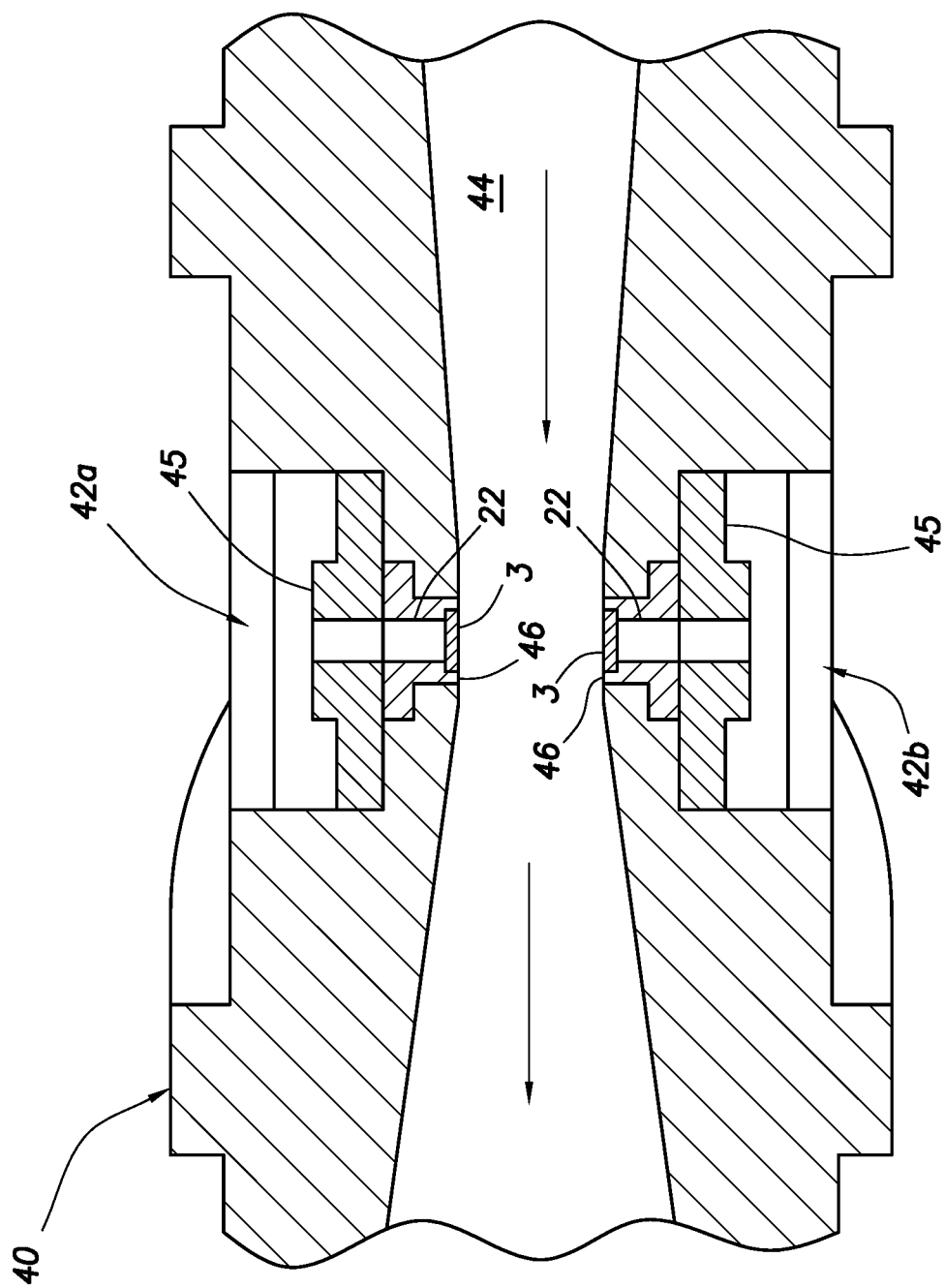
FIG. 5 depicts a perspective view of an implementation of the present disclosure.

A multi-window mounting assembly intended for mounting the ceramic window in a multiphase meter assembly 40 is shown in FIG. 5. Such flow meters are described in U.S. Pat. Nos. 6,265,713; 7,105,805; 6405,604; and 7,240,568 all assigned to the same assignee as the present patent application. In such flowmeter assembly 40, a pair of window assemblies 42a, 42b is arranged on opposite sides of a venturi passageway 44. Each of these window assemblies 42a, 42b includes a gamma-transparent plate 3 surrounded by and mounted within a tubular, metallic frame member 22 as previously described. Each of the metallic frame members 22 of the window assemblies 42a, 42b is sealingly connected to a multi-aperture window plate 45, which in turn is sealingly connected to the walls of the flow meter 40 on either side of the venturi passageway 44. An annular space 46 is provided between the outer surfaces of the tubular frame member 22 of each of the window assemblies 42a, 42b and the walls of the flowmeter 40. Each of these annular spaces 46 communicates with pressurized fluid flowing through the venture passageway 44 of the flow meter 40 so that pressurized fluid can contact the outer surfaces of the tubular frame members 22 and actuate the self-energizing feature of the present disclosure.

Embodiments of the present disclosure have been described in detail with particular reference to certain examples thereof, but it will be understood that variations, additions and modifications can be effected within the spirit and scope of the present invention as defined by the claims. All such variations, additions, modifications and equivalents thereof are encompassed within the scope of the present invention, which is limited only by the appended claims and all equivalents thereto.

The invention claimed is:

1. A gamma densitometer window, comprising:
   a plate of non-metallic material having a first face and a second face opposing one another and having an outer edge defined therebetween; and
   a metallic frame member fitted around the outer edge of the plate and adapted to pre-load the plate with a compressive stress that is sufficiently high such that a sum of the compressive stress, tensile stress and shear stress components generated in the plate under high-pressure conditions is always compressive.

2. The gamma densitometer window of claim 1, wherein the plate is circular, and the metallic frame member circumscribes the plate outer edge and substantially uniformly applies compressive stress around a circumference of the outer edge.

3. The gamma densitometer window of claim 2, wherein the metallic frame member includes a metallic tube having an inner diameter that circumscribes the outer edge of the plate.

4. The gamma densitometer window of claim 1, wherein pressurized fluid contacts an outer surface of the metallic frame member as well as the first face of the plate such that pressure from the fluid increases the compressive stress applied by the metallic frame member to the outer edge of the plate.

5. The gamma densitometer window of claim 3, wherein the metallic frame member includes an annular shoulder that supports an outer portion of the second face of the plate, wherein the second face is exposed to less pressure than the first face.

6. The gamma densitometer window of claim 5, wherein the metallic frame member includes an inner tube and an outer tube, wherein an end of the outer tube extends beyond an end of the inner tube, and the end of the outer tube circumscribes the outer edge of the plate.

7. The gamma densitometer window of claim 6, wherein the end of the inner tube forms the annular shoulder.

8. The gamma densitometer window of claim 3, further comprising a metal interface between the outer edge of the plate and the inner diameter of the metallic tube, wherein metal forming the interface is softer than metal forming the metallic tube.

9. The gamma densitometer window of claim 8, wherein the interface includes an annular support rim circumscribing an outer portion of the second face of the plate.

10. The gamma densitometer window of claim 3, wherein the metallic tube is formed from steel.

11. The gamma densitometer window of claim 1, wherein the non-metallic material forming the plate is substantially transparent to low-energy gamma radiation.

12. The gamma densitometer window of claim 11, wherein the non-metallic material includes one or more of boron carbide, boron nitride, silicon carbide, diamond, metal borides such as aluminum boride, magnesium boride, calcium boride, or titanium boride.

13. The gamma densitometer window of claim 1, wherein at least one of the first face and second face has a predetermined radius of curvature.

14. The gamma densitometer window of claim 1, wherein the gamma densitometer window is self-energizing, thereby providing increased compressive force against the plate.

15. The gamma densitometer window of claim 14, wherein the metallic frame member is mounted to a pressure bearing wall, such that a pressurized fluid confined by the pressure bearing wall further compresses the metallic frame member against the plate.

16. A method of fabricating a gamma densitometer window, comprising the steps of:
shrink-fitting a metallic frame member around an outer edge of a plate at a shrink-fit temperature such that the metallic frame member applies a compressive stress to the plate at any temperature below the shrink-fit temperature, wherein the compressive stress applied by the metallic frame member is sufficiently high such that a sum of compressive stress and tensile stress generated in the plate by pressure applied to the first face of the plate is always compressive; and
wherein the plate includes a non-metallic material having a first face and a second face opposing one another and has an outer edge defined therebetween, the metallic frame member having an inner periphery that is complementary in shape but smaller than the outer edge of the plate at an ambient temperature.

17. The fabrication method of claim 16, further including interposing a metal interface around the outer edge of the plate before shrink-fitting the metallic frame member around the outer edge.

18. The fabrication method of claim 17, wherein the metal forming the metal interface is softer than the metal forming the metallic frame member.

19. A multiphase flow meter, comprising:
a fluid conduit having a wall defining a passageway therethrough; and
a gamma densitometer window disposed in the wall, the gamma densitometer comprising:
a plate of non-metallic material having a first face and a second face opposing one another and having an outer edge defined therebetween; and
a metallic frame member fitted around the outer edge of the plate and adapted to pre-load the plate with a compressive stress that is sufficiently high such that a sum of the compressive stress, tensile stress and shear stress components generated in the plate under high-pressure conditions is always compressive.

20. The multiphase flow meter of claim 19, further comprising:
a space between the metallic frame member and the wall, wherein multiphase fluid flowing through the passageway flows into the space and compresses the metallic frame member when pressurized.

* * * * *